(12) United States Patent
Onishi et al.

(10) Patent No.: US 10,499,801 B2
(45) Date of Patent: *Dec. 10, 2019

(54) ENDOSCOPE REPROCESSOR

(71) Applicants: OLYMPUS CORPORATION, Tokyo (JP); HORIBA Advanced Techno, Co., Ltd., Kyoto-shi, Kyoto (JP)

(72) Inventors: Hideto Onishi, Hachioji (JP); Yoshihiko Kawaguchi, Kyoto (JP); Satoko Kai, Kyoto (JP)

(73) Assignees: OLYMPUS CORPORATION, Tokyo (JP); HORIBA Advanced Techno, Co., Ltd., Kyoto-shi, Kyoto (JP)

( * ) Notice: Subject to any disclaimer, the term of this patent is extended or adjusted under 35 U.S.C. 154(b) by 111 days.

This patent is subject to a terminal disclaimer.

(21) Appl. No.: 15/807,649

(22) Filed: Nov. 9, 2017

(65) Prior Publication Data

US 2018/0064325 A1    Mar. 8, 2018

Related U.S. Application Data

(63) Continuation of application No. PCT/JP2016/064486, filed on May 16, 2016.

(30) Foreign Application Priority Data

Jun. 2, 2015  (JP) ................ 2015-112490

(51) Int. Cl.
| | |
|---|---|
| *A61B 1/12* | (2006.01) |
| *G02B 23/24* | (2006.01) |
| *A61L 2/18* | (2006.01) |
| *B08B 9/023* | (2006.01) |
| *B08B 13/00* | (2006.01) |

(Continued)

(52) U.S. Cl.
CPC .......... *A61B 1/123* (2013.01); *A61B 1/00057* (2013.01); *A61B 1/125* (2013.01); *A61L 2/18* (2013.01); *A61L 2/24* (2013.01); *A61L 2/26* (2013.01); *B08B 9/023* (2013.01); *B08B 13/00* (2013.01); *G02B 23/24* (2013.01);
(Continued)

(58) Field of Classification Search
CPC ..................................................... A61B 1/121
See application file for complete search history.

(56) References Cited

FOREIGN PATENT DOCUMENTS

| | | |
|---|---|---|
| JP | 2003-075394 A | 3/2003 |
| JP | 2010-057792 A | 3/2010 |

(Continued)

OTHER PUBLICATIONS

International Search Report dated Jul. 19, 2016 issued in PCT/JP2016/064486.

(Continued)

*Primary Examiner* — Jason Y Ko
(74) *Attorney, Agent, or Firm* — Scully, Scott, Murphy & Presser P.C.

(57) ABSTRACT

An endoscope reprocessor includes a concentration sensor including a concave section in which a sensing section is housed and a permeable membrane configured to cover the concave section, a pressure resistant container in which the concentration sensor is housed, a medicinal-solution lead-in section configured to introduce a medicinal solution into the pressure resistant container, and a pressure adjusting section configured to adjust pressure such that an internal pressure of the concave section is low compared with an internal pressure of the pressure resistant container.

9 Claims, 9 Drawing Sheets

(51) Int. Cl.
*A61B 1/00* (2006.01)
*A61L 2/24* (2006.01)
*A61L 2/26* (2006.01)

(52) U.S. Cl.
CPC ....... *A61L 2202/14* (2013.01); *A61L 2202/17* (2013.01); *A61L 2202/24* (2013.01)

(56) References Cited

FOREIGN PATENT DOCUMENTS

| | | |
|---|---|---|
| JP | 2013-150954 A | 8/2013 |
| JP | 2014-100313 A | 6/2014 |

OTHER PUBLICATIONS

Extended Supplementary European Search Report dated Dec. 6, 2018 in European Patent Application No. 16 80 3031.0.

ENDOSCOPE REPROCESSOR

CROSS REFERENCE TO RELATED APPLICATION

This application is a continuation application of PCT/JP2016/064486 filed on May 16, 2016 and claims benefit of Japanese Application No. 2015-112490 filed in Japan on Jun. 2, 2015, the entire contents of which are incorporated herein by this reference.

BACKGROUND OF THE INVENTION

1. Field of the Invention

The present invention relates to an endoscope reprocessor including a concentration sensor including a concave section in which a sensing section is housed and a permeable membrane configured to cover the concave section.

2. Description of the Related Art

Medicinal solution treatment of an endoscope in which the endoscope reprocessor is used is performed by supplying a medicinal solution stored in a medicinal solution tank to a cleaning and disinfecting tub and immersing the endoscope in the medicinal solution at a set temperature for a predetermined time in the cleaning and disinfecting tub.

In order to surely perform the medicinal solution treatment of the endoscope, concentration control of medically effective components of the medicinal solution is important to prevent a medical effect from being deteriorated. This is because, in the medicinal solution, concentration of some medically effective components in the medicinal solution decreases from initial concentration because of repeated use and natural deterioration.

Note that, in the following explanation, concentration of a medically effective component in a medicinal solution is referred to as medicinal solution concentration. Therefore, in general, a check of the medicinal solution concentration is periodically performed in each medicinal solution treatment process of the endoscope.

As the check of the medicinal solution concentration, for example, there is a well-known method for confirming whether medicinal solution concentration is equal to or higher than effective concentration by, for example, sampling a medicinal solution from a medicinal solution tank, immersing test paper in the medicinal solution and observing a color change of the test paper, coloring the medicinal solution after the sampling, and measuring transmittance of light according to shades of colors using an absorbance meter and converting the medicinal solution concentration into a numerical value.

Japanese Patent Application Laid-Open Publication No. 2010-57792 discloses an endoscope reprocessor that can automatically confirm whether medicinal solution concentration is equal to or higher than effective concentration without separately sampling a medicinal solution because a concentration measuring device for the medicinal solution is provided in a medicinal solution tank, more specifically, an electrode is provided that is in contact with the medicinal solution and is applied with a constant voltage to thereby measure the medicinal solution concentration using an electrochemical reaction with the medicinal solution.

Therefore, a configuration of a concentration measuring device is also well-known in which, for example, in a medicinal solution tank, an electrode is provided in a concave section and the concave section is covered by a porous permeable membrane through which liquid does not permeate but only gas permeates, whereby organic matter and the like in the medicinal solution is prevented from adhering to the electrode by the permeable membrane.

In such a configuration of the concentration measuring device in which the permeable membrane is used, an internal solution different from the medicinal solution is sealed by the permeable membrane and is in contact with the permeable membrane in the concave section.

Therefore, when the permeable membrane is in contact with the medicinal solution, using a difference in component concentration between the medicinal solution and the internal solution, a medically effective component of the medicinal solution permeates through the permeable membrane making use of an osmotic pressure according to evaporation and mixes with the internal solution. As a result, the electrode can measure medicinal solution concentration via the internal solution.

FIG. 14 is a diagram schematically showing a state in which the internal solution and the medicinal solution permeate into the permeable membrane. FIG. 15 is a diagram schematically showing a state in which only the internal solution permeates into the permeable membrane.

When the medicinal solution is filled in the medicinal solution tank and a permeable membrane 10 is in contact with the medicinal solution, as shown in FIG. 14, the permeable membrane 10 has a three-layer structure in which a region 10a into which the medicinal solution permeates is formed on one surface side of the permeable membrane 10, a region 10c into which the internal solution permeates is formed on the other surface side of the permeable membrane 10, and a region 10b in which the permeable membrane 10 is dry is formed substantially in a center between the one surface and the other surface.

Therefore, the medically effective component in the medicinal solution evaporates from the region 10a, permeates through porosities of the region 10b, thereafter permeates into the region 10c, and thereafter mixes with the internal solution.

However, if the medicinal solution is let out from the medicinal solution tank and left untouched according to, for example, replacement of the medicinal solution in the medicinal solution tank, as shown in FIG. 15, the permeable membrane 10 changes to a two-layer structure of the region 10c into which the internal solution permeates and the dry region 10b including a size of the region 10a shown in FIG. 14.

SUMMARY OF THE INVENTION

An endoscope reprocessor according to an aspect of the present invention includes: a concentration sensor including a concave section in which a sensing section is housed and a permeable membrane configured to cover the concave section; a pressure resistant container in which the concentration sensor is housed; a medicinal-solution lead-in section configured to introduce a medicinal solution into the pressure resistant container; and a pressure adjusting section configured to adjust pressure such that an internal pressure of the concave section is low compared with an internal pressure of the pressure resistant container.

DETAILED DESCRIPTION OF THE PREFERRED EMBODIMENT(S)

Embodiments of the present invention are explained below with reference to the drawings. Note that the figures are schematic and relations between thicknesses and widths of respective members, ratios of the thicknesses of the respective members, and the like are different from real ones. It goes without saying that portions, relations and ratios of dimensions thereof are different, are included among the drawings. Note that, in the embodiments explained below, as concentration of a medicinal solution measured in a concentration measuring device included in an endoscope reprocessor, concentration of a disinfection solution, more specifically, concentration of peracetic acid in the disinfection solution is explained as an example.

First Embodiment

Figure 1:
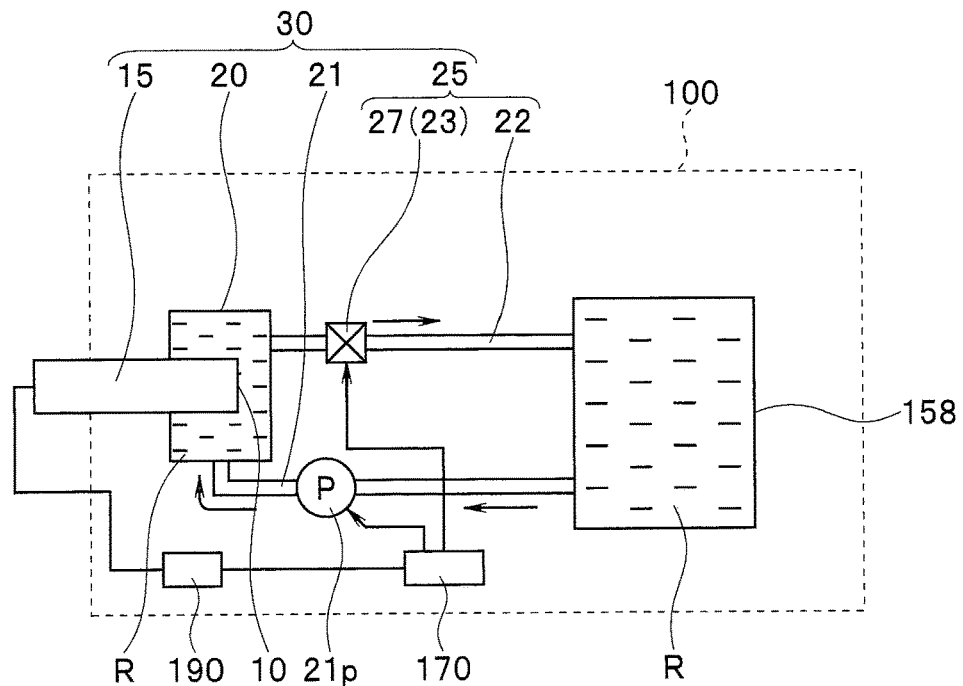
FIG. 1 is a diagram schematically showing a configuration of an endoscope reprocessor of a first embodiment.
Figure 2:
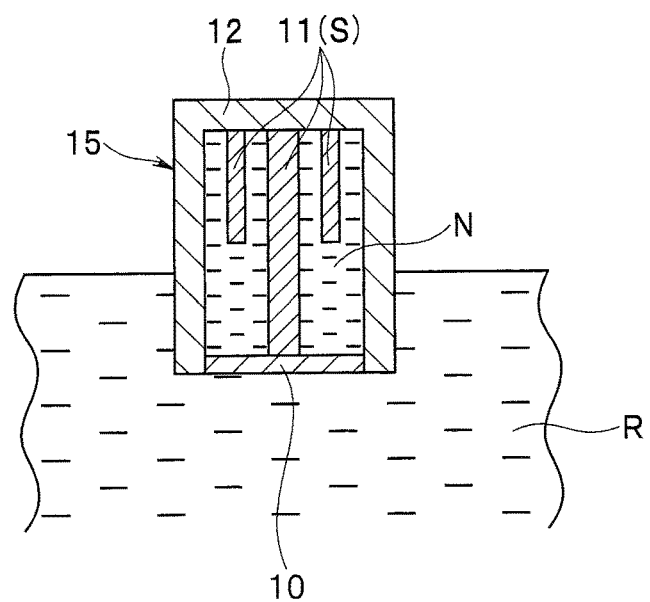
FIG. 2 is a partial sectional view showing a configuration of a concentration sensor shown in FIG. 1 together with a disinfection solution.

FIG. 1 is a diagram schematically showing a configuration of an endoscope reprocessor of a first embodiment. FIG. 2 is a partial sectional view showing a configuration of a concentration sensor shown in FIG. 1 together with a disinfection solution.

As shown in FIG. 1, an endoscope reprocessor 100 includes a concentration measuring device 30, a medicinal solution tank 158 in which a disinfection solution R is stored, and a control section 170.

A main part of the concentration measuring device 30 is configured by including a concentration sensor 15, a pressure resistant container 20 in which the concentration sensor 15 is housed, a medicinal-solution lead-in section 21 configured to introduce the disinfection solution R into the pressure resistant container 20, a pressure adjusting section configured to adjust an internal pressure of the concentration sensor 15 to be lower than an internal pressure of the pressure resistant container 20, and a concentration measuring section 190.

Note that the concentration measuring device 30 of the first embodiment includes, as the pressure adjusting section, a pressurizing section 25 configured to increase the internal pressure of the pressure resistant container 20 to a predetermined pressure.

The concentration sensor 15 includes, as shown in FIG. 2, a concave section 12 in which a sensing section S is housed and a permeable membrane 10 configured to cover the concave section 12.

As explained above, the permeable membrane 10 is configured of a material having porosities through which liquid does not permeate and only gas permeates. Note that examples of the material configuring the permeable membrane 10 include silicone.

An inside of the concave section 12 may be a hollow section. However, when an electrode 11 configured to measure concentration of a detection target is used as the sensing section S, it is desirable that an internal solution N different from the disinfection solution R is sealed in the concave section 12 by the permeable membrane 10.

A composition of the internal solution is not particularly limited and can be determined as appropriate according to a detection target. For example, when peracetic acid concentration in a peracetic acid mixed solution is detected, as the internal solution, for example, a phosphate buffer solution, an acetic acid buffer solution, tris hydroxymethyl aminomethane, a boric acid buffer solution, or a citrate buffer solution can be used.

Using a difference in component concentration between the disinfection solution R and the internal solution N, peracetic acid in the disinfection solution R permeates through the permeable membrane 10 making use of an osmotic pressure according to evaporation and mixes in the internal solution N, whereby the concentration measuring section 190 measures, according to driving control by the control section 170, peracetic acid concentration via the internal solution N using an electrochemical reaction between the electrode 11, to which a voltage is applied from the concentration measuring section 190, and the internal solution N. The voltage applied to the electrode 11 is not particularly limited but may be, for example, a constant voltage.

Figure 14:
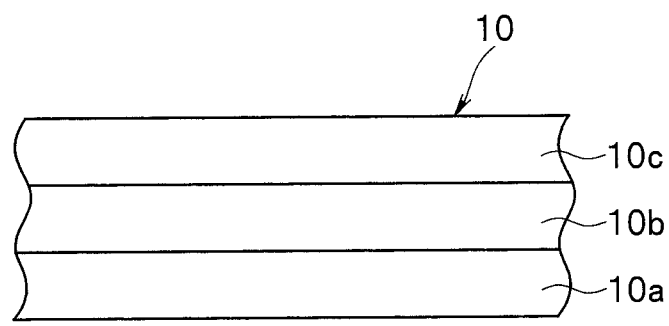
FIG. 14 is a diagram schematically showing a state in which an internal solution and a medicinal solution permeate into a permeable membrane.
Figure 15:
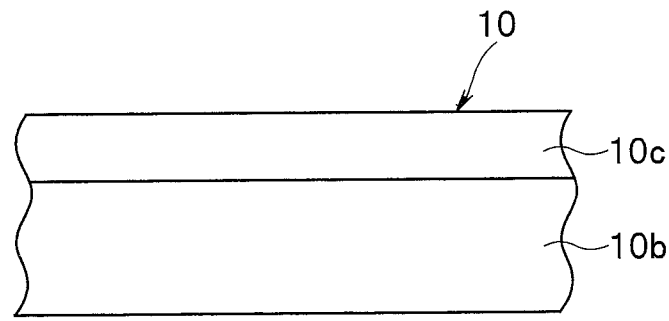
FIG. 15 is a diagram schematically showing a state in which only the internal solution permeates into the permeable membrane.

Note that, on one hand, in a state in which the disinfection solution R is led into the pressure resistant container 20 and is in contact with the disinfection solution R as shown in FIG. 2, as shown in FIG. 14 referred to above, the permeable membrane 10 has the three-layer structure including the regions 10a, 10b, and 10c. On the other hand, when the disinfection solution R is not led into the pressure resistant container 20, as shown in FIG. 15 referred to above, the permeable membrane 10 is dry and has the two-layer structure including only the regions 10b and 10c.

Referring back to FIG. 1, the medicinal-solution lead-in section 21 is a conduit configured to connect the medicinal solution tank 158 and the pressure resistant container 20 and introduce the disinfection solution R in the medicinal solution tank 158 into the pressure resistant container 20.

More specifically, a medicinal-solution transfer section 21p configured to transfer the disinfection solution R in the medicinal solution tank 158 is provided in a halfway position of the medicinal-solution lead-in section 21. The disinfection solution R in the medicinal solution tank 158 is supplied into the pressure resistant container 20 according to driving of the medicinal-solution transfer section 21p involved in the driving control by the control section 170. Note that the medicinal-solution transfer section 21p is configured of, for example, a pump.

A main part of the pressurizing section 25 is configured by a medicinal-solution lead-out section 22 provided in the pressure resistant container 20 and a flow-rate limiting section 27 provided in the medicinal-solution lead-out section 22.

The medicinal-solution lead-out section 22 is a conduit configured to connect the pressure resistant container 20 and the medicinal solution tank 158 and return the disinfection solution R in the pressure resistant container 20 into the medicinal solution tank 158.

The flow-rate limiting section 27 only has to be capable of limiting a flow rate of fluid led out from the pressure resistant container. For example, an electromagnetic valve, an electropneumatic proportional valve, or means for, for example, preparing and switching a plurality of conduits having different diameters or preparing a plurality of conduits and closing a predetermined number of conduits can be used.

In the present embodiment, an example in which the electromagnetic valve is used is explained. An electromagnetic valve 27 opens and closes a channel of the medicinal-solution lead-out section 22 according to the driving control by the control section 170.

Therefore, when the electromagnetic valve 27 is opened and the medicinal-solution transfer section 21p is driven, the disinfection solution R circulates between the medicinal solution tank 158 and the pressure resistant container 20 via the medicinal-solution lead-in section 21 and the medicinal-solution lead-out section 22.

When the peracetic acid permeates through the permeable membrane 10 and mixes with the internal solution N, the peracetic acid included in the disinfection solution R near the permeable membrane 10 decreases. Therefore, it is desirable that the disinfection solution R continues to circulate during measurement of concentration such that a new disinfection solution R can always be led into the pressure resistant container 20. This is because, if the disinfection solution R does not circulate, peracetic acid concentration in the pressure resistant container 20 continues to decrease and accurate concentration measurement cannot be performed.

In a state in which the electromagnetic valve 27 is closed, the disinfection solution R is supplied into the pressure resistant container 20 by the driving of the medicinal-solution transfer section 21p, whereby the pressurizing section 25 raises an internal pressure of the pressure resistant container 20 to the predetermined pressure. Consequently, the internal pressure of the pressure resistant container 20 is higher than an internal pressure of the concave section 12 of the concentration sensor 15.

However, the electromagnetic valve 27 may be completely closed or a flow rate of the electromagnetic valve 27 only has to be reduced. The flow rate of the fluid led out from the pressure resistant container is limited by the flow-rate limiting section to be smaller than a flow rate of a medicinal solution led into the pressure resistant container from a medicinal-solution supply section, whereby the internal pressure of the pressure resistant container 20 rises.

As a result, the disinfection solution R in the pressure resistant container 20 is pressed against the permeable membrane 10 by pressure. Therefore, the disinfection solution R more quickly permeates into the permeable membrane 10 than usual.

Note that, when it is detected by a not-shown pressure gauge provided in the pressure resistant container 20 that the internal pressure of the pressure resistant container 20 is equal to or higher than the predetermined pressure, the control section 170 performs control for opening the electromagnetic valve 27.

In this way, in the present embodiment, the concentration measuring device 30 is explained as including the pressurizing section 25.

Therefore, even if the permeable membrane 10 dries out, it is possible to quickly start concentration measurement by raising the internal pressure of the pressure resistant container 20 with the pressurizing section 25.

It is surmised that an effect explained below is produced when the concentration sensor is immersed in the disinfection solution in a pressurized state compared with when the concentration sensor is immersed in the disinfection solution in a non-pressurized state.

When the disinfection solution R is pressurized, since the disinfection solution R is pressed into the permeable membrane 10, it is possible to more quickly return the permeable membrane 10 from a state shown in FIG. 15 to a state shown in FIG. 14 than causing the disinfection solution to permeate without pressurizing the disinfection solution.

Further, it is surmised that an effect explained below is also produced depending on a pressure value.

Since solubility of a peracetic acid gas increases according to application of pressure to the disinfection solution, it is possible to prevent air bubbles from occurring from the peracetic acid. When air bubbles occur and adhere to the permeable membrane, it is likely that peracetic acid solution permeation in an adhering portion is hindered.

Therefore, even after the disinfection solution R is injected into the medicinal solution tank 158, it is possible to quickly and accurately perform the concentration measurement of the disinfection solution R.

The concentration measurement of the disinfection solution R performed using the concentration sensor 15 can be performed in the pressure resistant container 20 different from the medicinal solution tank 158. Therefore, in the endoscope reprocessor 100, the pressure resistant container 20 can be disposed in a free position. Therefore, for example, if the pressure resistant container 20 is disposed in an upper part of the endoscope reprocessor 100, it is easy to perform replacement work of the concentration sensor 15.

Consequently, it is possible to provide the concentration measuring device 30 and the endoscope reprocessor 100 including a configuration that can cause the disinfection solution R to quickly permeate into the dried permeable membrane 10 and can quickly and accurately measure medicinal solution concentration.

A modification is explained below. In the present embodiment explained above, the electromagnetic valve 27 is opened and closed by the control section 170.

Independently of this, the electromagnetic valve 27 may be configured of a relief valve 23 that is usually closed and is opened when the internal pressure of the pressure resistant container 20 is equal to or higher than the predetermined pressure.

By fixing pressure applied to the permeable membrane 10, it is possible to stabilize permeation speed of the disinfection solution R into the permeable membrane 10 and permeation speed of the peracetic acid through the permeable membrane 10. As a result, it is possible to stabilize accuracy of concentration measurement performed using the electrode 11.

If the electromagnetic valve 27 is configured of the relief valve 23, the internal pressure of the pressure resistant container 20 after the medicinal-solution transfer section 21p driving is stabilized to the predetermined pressure. Therefore, there is an advantage that the accuracy of the concentration measurement performed using the electrode 11 is stabilized.

Note that, instead of the relief valve 23, an orifice configured to stabilize the internal pressure of the pressure resistant container 20 after the medicinal-solution transfer section 21p driving to the predetermined pressure may be provided in the medicinal-solution lead-out section 22.

Figure 3:
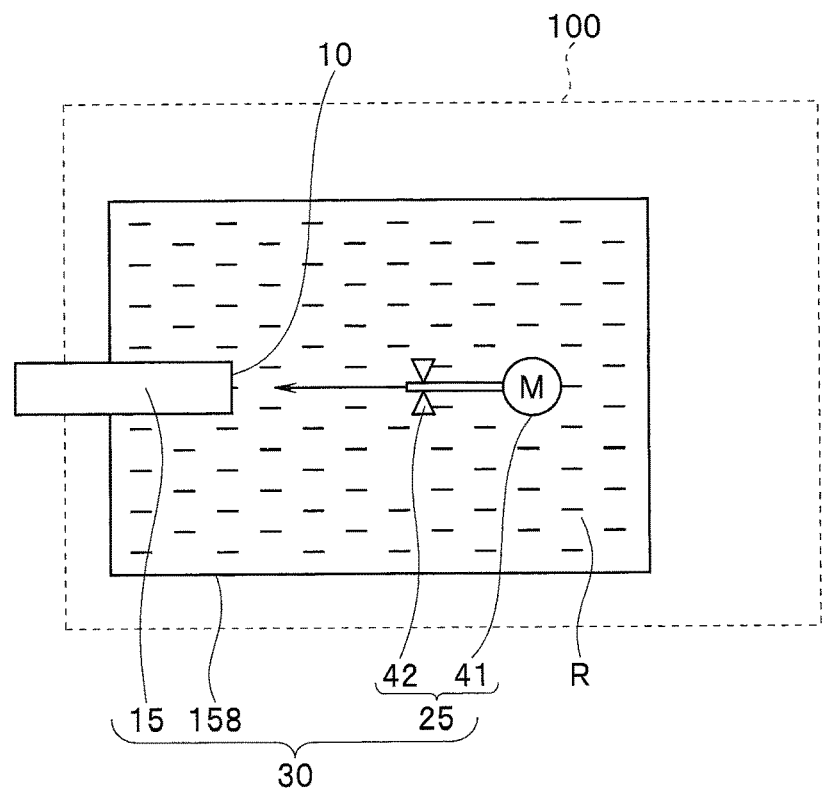
FIG. 3 is a diagram schematically showing a modification in which the concentration sensor is provided in a medicinal solution tank shown in FIG. 1.

Another modification is explained below with reference to FIG. 3. FIG. 3 is a diagram schematically showing a modification in which the concentration sensor is provided in the medicinal solution tank shown in FIG. 1.

In the present embodiment explained above, the concentration sensor 15 is explained as being provided in the pressure resistant container 20.

Different from this, as shown in FIG. 3, the concentration sensor 15 may be provided in the medicinal solution tank 158.

Specifically, as shown in FIG. 3, the main part of the concentration measuring device 30 may be configured of the medicinal solution tank 158, the concentration sensor 15, and the pressurizing section 25. The concentration sensor 15 and the pressurizing section 25 may be provided in the medicinal solution tank 158.

The pressurizing section 25 includes a motor 41 and a propeller 42 turned by the motor 41. The propeller 42 is turned according to driving of the motor 41, whereby the disinfection solution R in the medicinal solution tank 158 is pressed against the permeable membrane 10 by applying pressure to the disinfection solution R with a water flow and the disinfection solution R in the medicinal solution tank 158 is circulated.

In such a configuration, it is also possible to cause the disinfection solution R to quickly permeate into the dried permeable membrane 10. Therefore, it is possible to obtain the same effects as the effects in the present embodiment explained above.

Note that another modification is explained below. In the present embodiment explained above, the main part of the pressurizing section 25 configured to increase the internal pressure of the pressure resistant container 20 to the predetermined pressure is configured by the medicinal-solution lead-out section 22 provided in the pressure resistant container 20 and the electromagnetic valve 27 provided in the medicinal-solution lead-out section 22. However, the pressurizing section 25 may have another configuration. Another configuration of the pressurizing section 25 is explained below with reference to FIGS. 4 to 8.

Figure 4:
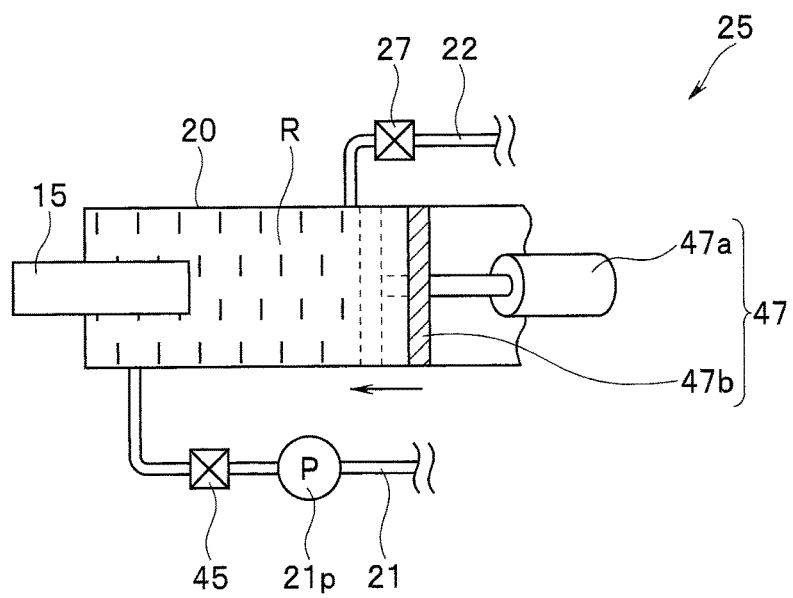
FIG. 4 is a diagram schematically showing a modification in which a pressurizing section including an actuator is provided in a pressure resistant container shown in FIG. 1.

FIG. 4 is a diagram schematically showing a modification in which a pressurizing section including an actuator is provided in the pressure resistant container shown in FIG. 1.

As shown in FIG. 4, the pressurizing section 25 may include an actuator 47 in which a sealing member 47b provided in the pressure resistant container 20 moves according to driving of a motor 47a. Note that the actuator 47 is controlled to be driven by the control section 170.

Note that, in this configuration of the pressurizing section 25, in the medicinal-solution lead-in section 21, an electromagnetic valve 45 controlled to be opened and closed by the control section 170 is provided on the pressure resistant container 20 side with respect to the medicinal-solution transfer section 21p. Note that the electromagnetic valve 45 may be configured of a check valve.

With such a configuration, if the electromagnetic valves 45 and 27 are closed and the actuator 47 is driven to move the sealing member 47b to reduce a capacity in the pressure resistant container 20, the internal pressure of the pressure resistant container 20 rises.

Figure 5:
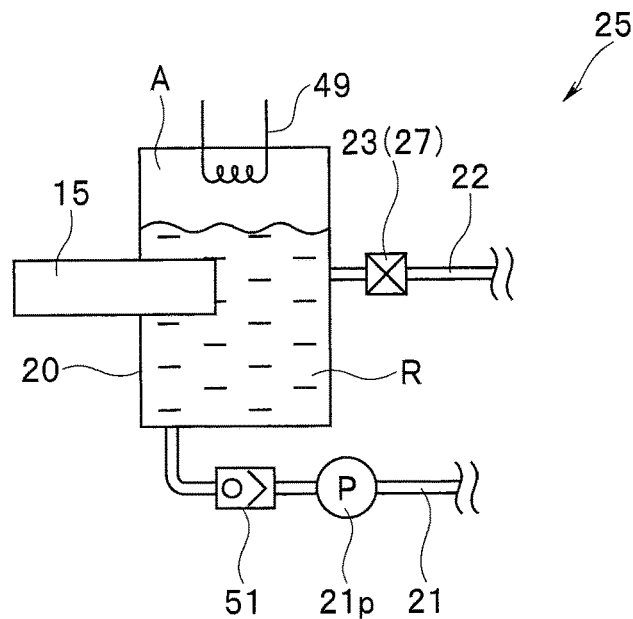
FIG. 5 is a diagram schematically showing a modification in which a pressurizing section including a heater is provided in the pressure resistant container shown in FIG. 1.

FIG. 5 is a diagram schematically showing a modification in which the pressurizing section including a heater is provided in the pressure resistant container shown in FIG. 1.

As shown in FIG. 5, the pressurizing section 25 may include a heater 49 configured to heat an inside of the pressure resistant container 20 according to the driving control by the control section 170.

Note that, in this configuration of the pressurizing section 25, in the medicinal-solution lead-in section 21, a check valve 51 is provided on the pressure resistant container 20 side with respect to the medicinal-solution transfer section 21p.

With such a configuration, if gas A or the disinfection solution R in the pressure resistant container 20 is heated by the heater 49, since volume of the gas A increases, the internal pressure of the pressure resistant container 20 rises.

Figure 6:
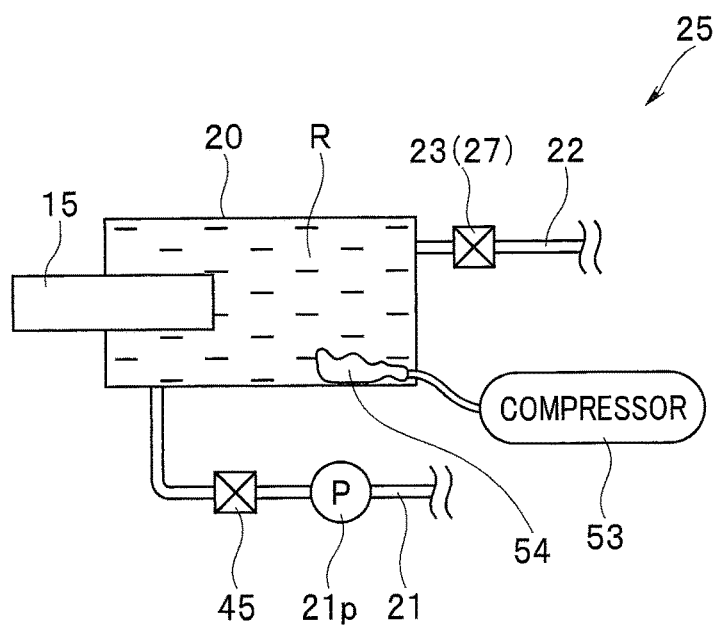
FIG. 6 is a diagram schematically showing a modification in which a pressurizing section including an airbag is provided in the pressure resistant container shown in FIG. 1.

FIG. 6 is a diagram schematically showing a modification in which the pressurizing section including an airbag is provided in the pressure resistant container shown in FIG. 1.

As shown in FIG. 6, the pressurizing section 25 may include an airbag 54 provided in the pressure resistant container 20 and expanded by air feeding from a compressor 53 controlled to be driven by the control section 170.

Note that, in this configuration of the pressurizing section 25, in the medicinal-solution lead-in section 21, as in FIG. 4, the electromagnetic valve 45 is provided on the pressure resistant container 20 side with respect to the medicinal-solution transfer section 21p.

With such a configuration, if the electromagnetic valves 45 and 27 are closed and the compressor 53 is driven to expand the airbag 54, the internal pressure of the pressure resistant container 20 rises.

Figure 7:
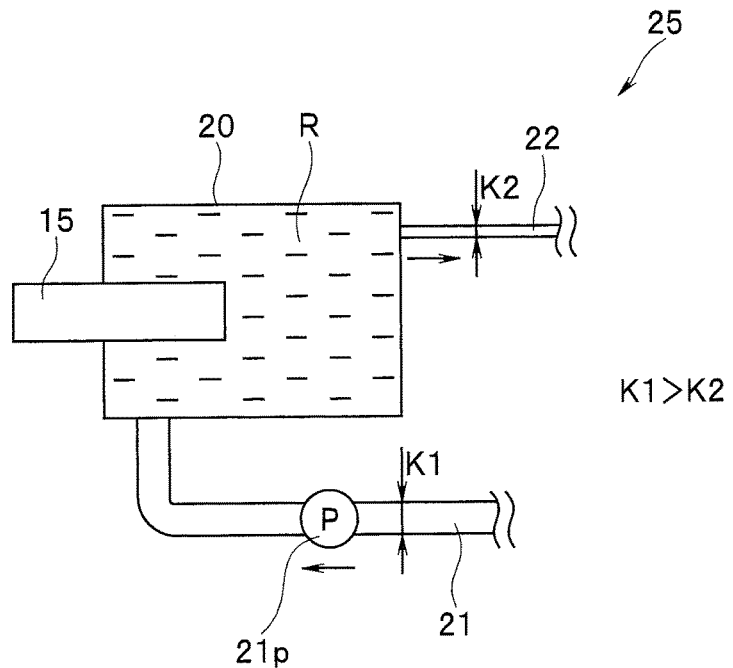
FIG. 7 is a diagram schematically showing a configuration of a modification of a pressurizing section in which a diameter of a medicinal-solution lead-out section shown in FIG. 1 is set smaller than a diameter of a medicinal-solution lead-in section shown in FIG. 1 to vary a supply pressure of a medicinal-solution transfer section.

FIG. 7 is a diagram schematically showing a configuration of a modification of the pressurizing section in which a diameter of the medicinal-solution lead-out section shown in FIG. 1 is set smaller than a diameter of the medicinal-solution lead-in section shown in FIG. 1 to vary a supply pressure of the medicinal-solution transfer section.

As shown in FIG. 6, the pressurizing section 25 may have a configuration in which a conduit diameter K2 of the medicinal-solution lead-out section 22 is set smaller than a conduit diameter K1 of the medicinal-solution lead-in section 21 (K2<K1) and a supply pressure of the medicinal-solution transfer section 21p is varied.

With such a configuration, when pressurization in the pressure resistant container 20 is unnecessary, the medicinal-solution transfer section 21p is driven at a first supply pressure at which the disinfection solution R sufficiently permeates through the medicinal-solution lead-out section 22. When pressurizing in the pressure resistant container 20 is necessary, if the medicinal-solution transfer section 21p is driven at a second supply pressure larger than the first supply pressure, the medicinal-solution lead-out section 22 functions as an orifice. Therefore, the internal pressure of the pressure resistant container 20 rises.

Figure 8:
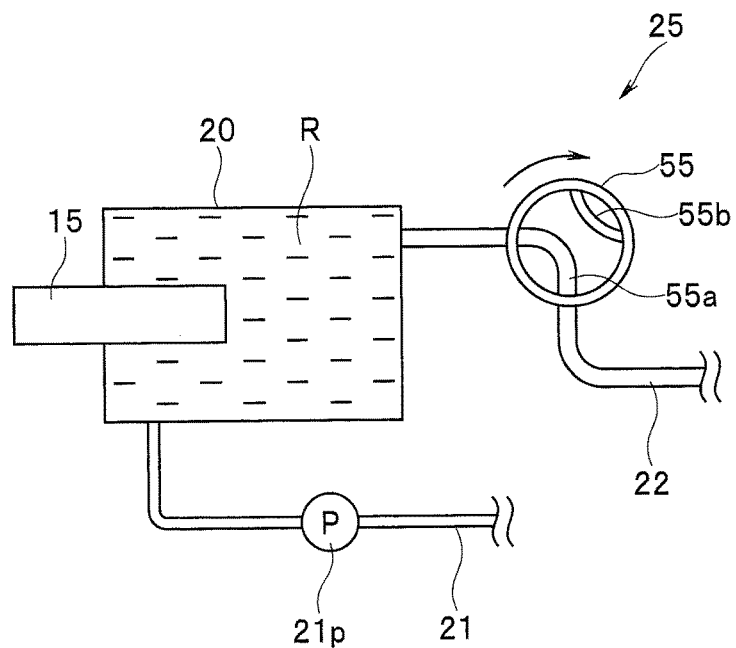
FIG. 8 is a diagram schematically showing a modification in which a pressurizing section including an outflow-resistance varying member is provided in the medicinal-solution lead-out section shown in FIG. 1.

FIG. 8 is a diagram schematically showing a modification in which the pressurizing section including an outflow-resistance varying member is provided in the medicinal-solution lead-out section shown in FIG. 1.

As shown in FIG. 8, the pressurizing section 25 may include an outflow-resistance varying member 55 provided in the medicinal-solution lead-out section 22.

The outflow-resistance varying member 55 is configured to be capable of turning according to the driving control by the control section 170 and configured of a ball valve including a large-diameter conduit 55a and a small-diameter conduit 55b.

With such a configuration, when pressurization in the pressure resistant container 20 is unnecessary, the outflow-resistance varying member 55 causes the conduit 55a to communicate with the medicinal-solution lead-out section 22. When pressurization in the pressure resistant container 20 is necessary, the outflow-resistance varying member 55 turns and causes the conduit 55b to communicate with the medicinal-solution lead-out section 22. Consequently, since the conduit 55b functions as an orifice, the internal pressure of the pressure resistant container 20 rises.

Note that a configuration of the outflow-resistance varying member 55 configured to vary a channel diameter of the medicinal-solution lead-out section 22 is not limited to the ball valve shown in FIG. 8 and may be an electric needle valve or the like.

Although not shown in the figure, the pressurizing section 25 may be configured to provide a small hole in the electromagnetic valve 27 and, when the electromagnetic valve 27 is closed, cause the small hole to function as an orifice.

Second Embodiment

Figure 9:
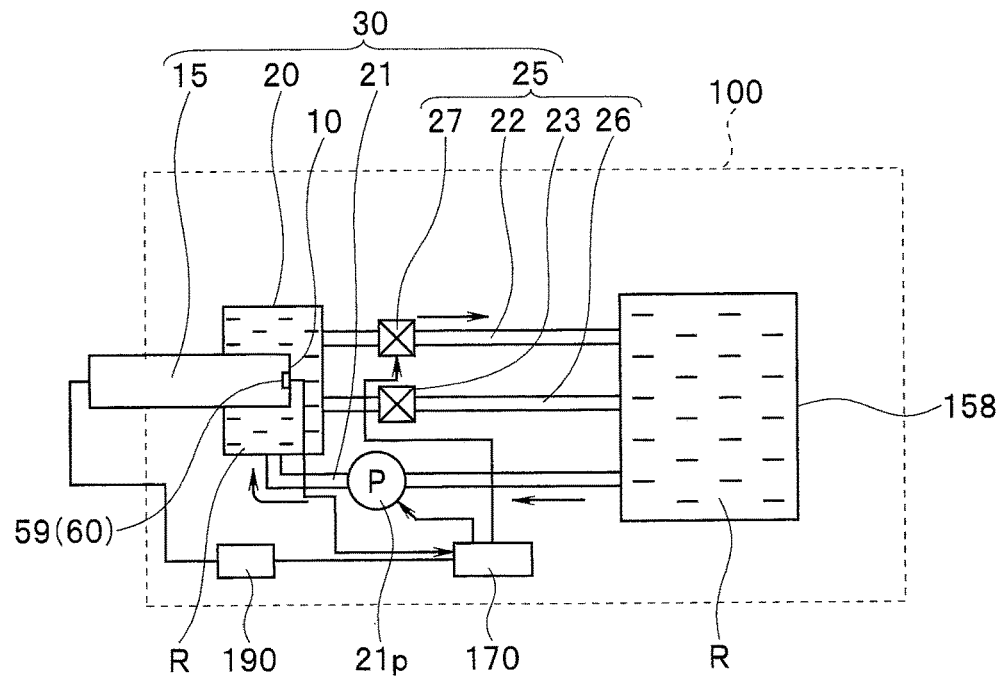
FIG. 9 is a diagram schematically showing a configuration of an endoscope reprocessor of a second embodiment.

FIG. 9 is a diagram schematically showing a configuration of an endoscope reprocessor of a second embodiment.

Configurations of a concentration measuring device and the endoscope reprocessor of the second embodiment are different in that a dryness degree of the permeable membrane is detected and the internal pressure of the pressure resistant container is raised only when the permeable membrane is dry compared with the configurations of the concentration measuring device and the endoscope reprocessor in the first embodiment shown in FIG. 1 and FIG. 2.

Therefore, the same components as the components in the first embodiment are denoted by the same reference numerals and signs and explanation of the components is omitted.

In the following explanation, a configuration for raising the internal pressure of the pressure resistant container 20 only in a state in which the permeable membrane 10 does not reach a target temperature as shown in FIG. 15 is explained with reference to FIG. 9.

As shown in FIG. 9, in this embodiment, a main part of the pressurizing section 25 is configured by, in addition to the medicinal-solution lead-out section 22 provided in the pressure resistant container 20 and the electromagnetic valve 27 provided in the medicinal-solution lead-out section 22, a medicinal-solution lead-out section 26 provided in the pressure resistant container 20 and the relief valve 23 provided in the medicinal-solution lead-out section 26.

Note that the configuration of the pressurizing section 25 may be the configuration shown in FIG. 4 to FIG. 8 as in the first embodiment explained above.

In the pressure resistant container 20, a dryness detecting section 60 configured to detect a dryness degree of the permeable membrane 10 and electrically connected to the control section 170 is provided. The dryness detecting section 60 is connected to a determining section configured to determine from a detection result of the dryness detecting section 60 whether the permeable membrane reaches a dry state.

Note that, in this embodiment, as the dryness detecting section 60, a hydrometer 59 provided in the permeable membrane 10 is explained as an example.

As in the first embodiment, the control section 170 performs open/close control of the electromagnetic valve 27. When it is determined by the determining section that the permeable membrane reaches the dry state, the control section 170 performs control for closing the electromagnetic valve 27.

When the hydrometer 59 is used as the dryness detecting section 60, if humidity is equal to or smaller than a predetermined value, the determining section determines that the permeable membrane reaches the dry state.

When a not-shown clocking device is used as the dryness detecting section 60, a time period after the medicinal solution is discharged from the pressure resistant container, that is, a time period in which the permeable membrane is exposed to air is measured. If the time period exceeds a predetermined time period, the determining section determines that the permeable membrane reaches the dry state.

Note that the other components are the same as the components of the first embodiment explained above.

With such a configuration, when the hydrometer 59 detects that the dryness degree of the permeable membrane 10 is smaller than a reference value, that is, in a state in which the permeable membrane 10 is in contact with the disinfection solution R as shown in FIG. 14 referred to above, since it is unnecessary to apply pressure to the permeable membrane 10, the control section 170 opens the electromagnetic valve 27.

Consequently, the disinfection solution R circulates between the pressure resistant container 20 and the medicinal solution tank 158 via the medicinal-solution lead-in section 21 and the medicinal-solution lead-out section 22 according to the driving of the medicinal-solution transfer section 21p.

Subsequently, when the hydrometer 59 detects that the dryness degree of the permeable membrane 10 is equal to or larger than the reference value, that is, in a state in which the permeable membrane 10 is dry as shown in FIG. 15 referred to above, as in the first embodiment, in order to cause the disinfection solution R to quickly permeate into the permeable membrane 10, the pressurizing section 25 raises the internal pressure of the pressure resistant container 20. More specifically, the control section 170 closes the electromagnetic valve 27.

As a result, the internal pressure of the pressure resistant container 20 rises. However, since the relief valve 23 opens when the internal pressure reaches the predetermined pressure, the pressure resistant container 20 is maintained at the predetermined pressure. At this point, the disinfection solution R circulates between the pressure resistant container 20 and the medicinal solution tank 158 via the medicinal-solution lead-in section 21 and the medicinal-solution lead-out section 26 according to the driving of the medicinal-solution transfer section 21p.

Therefore, it is possible to obtain the same effects as the effects in the first embodiment. Besides, since the pressurizing section 25 pressurizes the inside of the pressure resistant container 20 only when it is detected by the hydrometer 59 that the permeable membrane 10 is dry. Therefore, it is possible to delay deterioration of the permeable membrane 10.

It is possible to further reduce thickness of the permeable membrane 10. As the permeable membrane 10 is further reduced in thickness, there is an advantage that it is possible to reduce a reaching time of peracetic acid to an electrode and it is possible to reduce a concentration measurement time.

Figure 11:
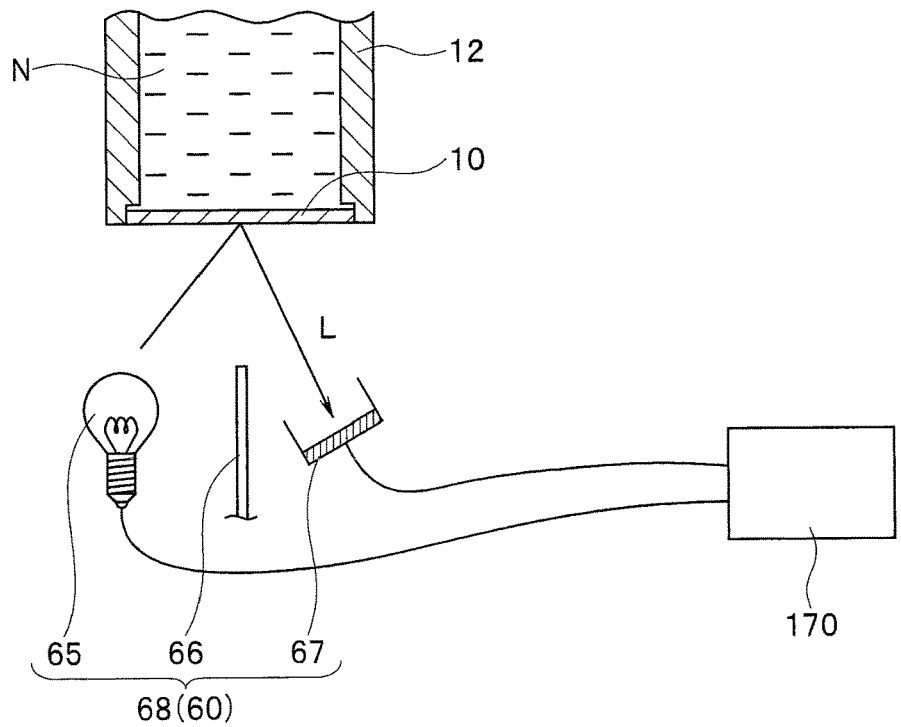
FIG. 11 is a partial sectional view schematically showing a modification in which the dryness detecting section shown in FIG. 9 is configured of a photodetector.
Figure 12:
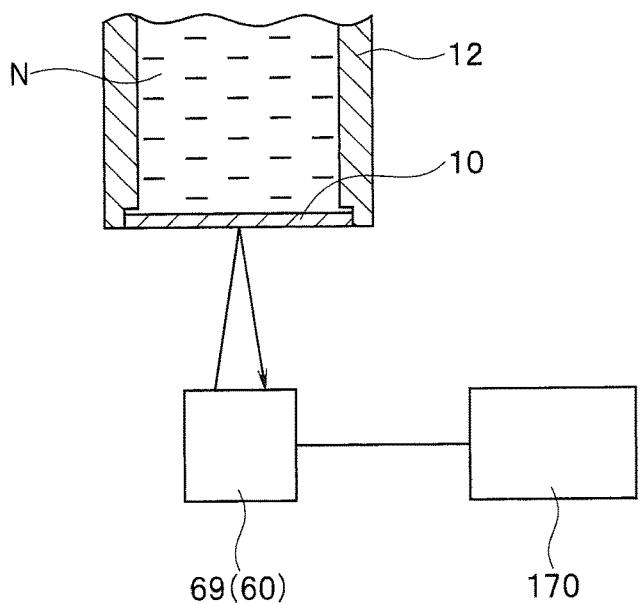
FIG. 12 is a partial sectional view schematically showing a modification in which the dryness detecting section shown in FIG. 9 is configured of a temperature detector.

Note that, in the present embodiment explained above, the hydrometer 59 is explained as the example of the dryness detecting section 60. Besides, configurations shown in FIG. 10 to FIG. 12 are conceivable.

Figure 10:
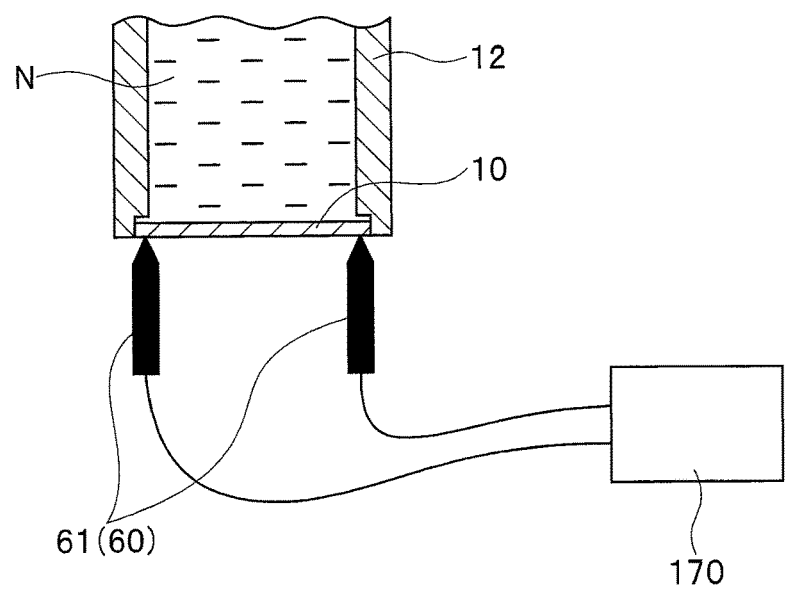
FIG. 10 is a partial sectional view schematically showing a modification in which a dryness detecting section shown in FIG. 9 is configured of an electrode.

FIG. 10 is a partial sectional view schematically showing a modification in which the dryness detecting section shown in FIG. 9 is configured of an electrode.

As shown in FIG. 10, the dryness detecting section 60 may be configured of an electrode 61 electrically connected to the control section 170, in contact with the permeable membrane 10, and configured to energize the permeable membrane 10.

With such a configuration, if resistance of the permeable membrane 10 is measured according to energization from the electrode 61, it is possible to detect a dryness degree of the permeable membrane 10.

FIG. 11 is a partial sectional view schematically showing a modification in which the dryness detecting section shown in FIG. 9 is configured of a photodetector.

As shown in FIG. 11, the dryness detecting section 60 may be configured of a photodetector 68 electrically connected to the control section 170.

The photodetector 68 is configured of a light emitting section 65 configured to irradiate light on the permeable membrane 10, a light receiving section 67 configured to receive reflected light from the permeable membrane 10, and a shielding plate 66 configured to shield the light emitting section 65 and the light receiving section 67.

With such a configuration, it is possible to detect a dryness degree of the permeable membrane 10 from reflectance of light detected by the light receiving section 67.

FIG. 12 is a partial sectional view schematically showing a modification in which the dryness detecting section shown in FIG. 9 is configured of a temperature detector.

As shown in FIG. 12, the dryness detecting section 60 may be configured of a temperature detector 69 electrically connected to the control section 170.

The temperature detector 69 irradiates an infrared ray on the permeable membrane 10 and detects infrared light reflected from the permeable membrane 10.

With such a configuration, when the permeable membrane 10 is wet, temperature is detected low because of evaporation of the disinfection solution R. When the permeable membrane 10 is dry, temperature is detected high. Therefore, it is possible to detect a dryness degree of the permeable membrane 10.

Note that, as other configurations of the dryness detecting section 60, it is conceivable to adopt, for example, a configuration in which a water level gauge is provided in the pressure resistant container 20 and it is determined from a water level in the pressure resistant container 20 whether the permeable membrane 10 is in contact with the disinfection solution R and a configuration in which a water level in the pressure resistant container 20 and a water level in the medicinal solution tank 158 are set to the same water level and it is determined from a water level gauge provided in the medicinal solution tank 158 whether the permeable membrane 10 is in contact with the disinfection solution R.

An example of the configurations of the endoscope reprocessor 100 in the first and second embodiments explained above is explained with reference to FIG. 13.

Figure 13:
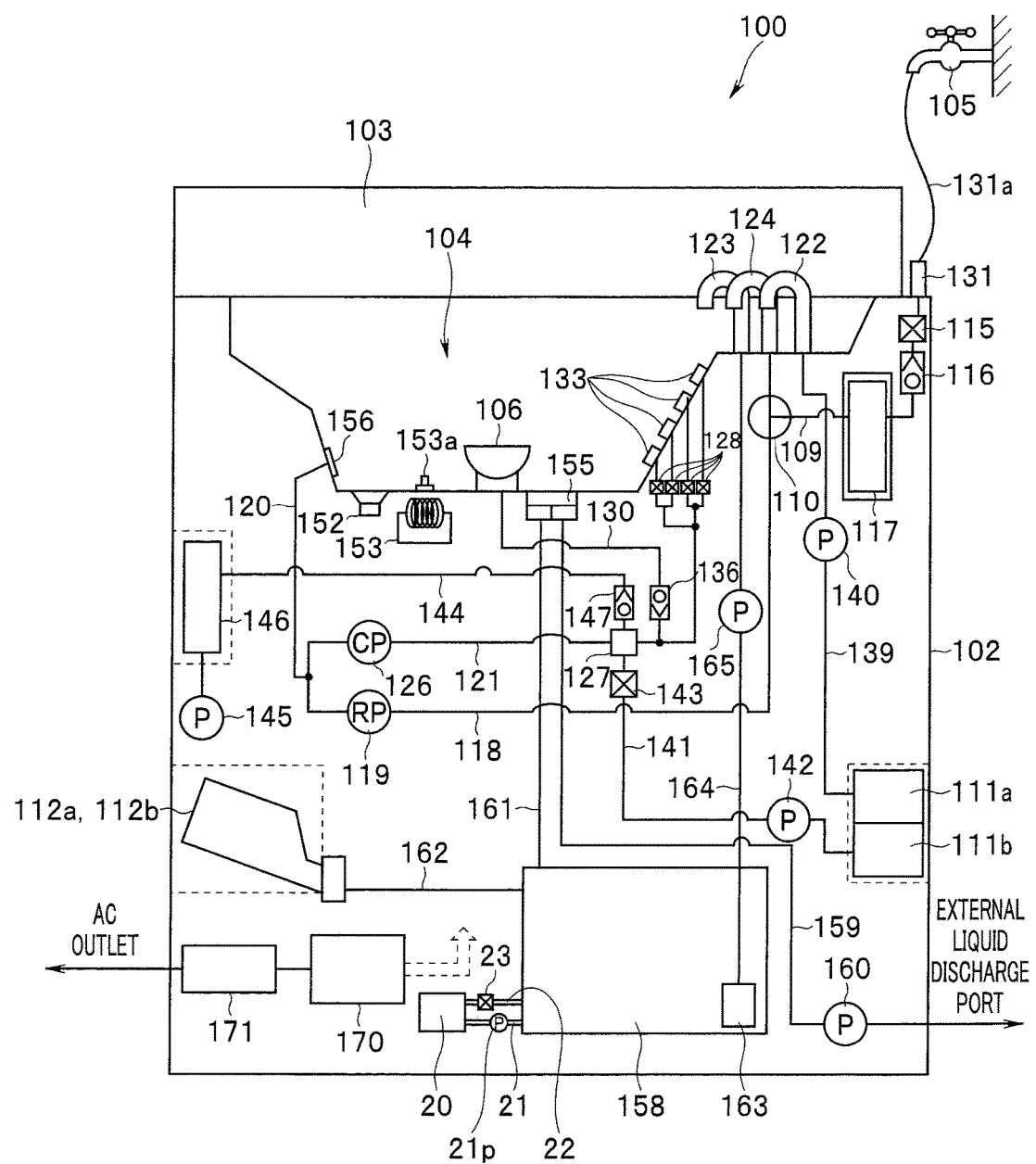
FIG. 13 is a diagram showing an example of an internal configuration of the endoscope reprocessor.

FIG. 13 is a diagram showing an example of an internal configuration of the endoscope reprocessor.

As shown in FIG. 13, the endoscope reprocessor 100 is a device for cleaning and disinfecting a used endoscope. A main part of the endoscope reprocessor 100 is configured by an apparatus main body 102 and a top cover 103 openclosably connected to an upper part of the apparatus main body 102 via, for example, a not-shown hinge.

In the endoscope reprocessor 100, a water-supply-hose connection port 131, to which a faucet 105 is connected via a tube 131a, communicates with one end of a water supply conduit 109. The other end of the water supply conduit 109 is connected to a three-way electromagnetic valve 110. A water-supply electromagnetic valve 115, a check valve 116, and a water supply filter 117 are interposed in order from the water-supply-hose connection port 131 side halfway in the conduit.

Note that the water supply filter 117 is configured as a filtration filter of a cartridge type to be capable of being periodically replaced. The water supply filter 117 removes foreign matter, germs, and the like of tap water passing though the water supply filter 117.

The three-way electromagnetic valve 110 is connected to one end of a liquid flow conduit 118 and switches, with a valve on an inside, communication of the water supply conduit 109 and the liquid flow conduit 118 with a water-supply circulation nozzle 124. That is, the water-supply circulation nozzle 124 communicates with at least one of the water supply conduit 109 and the liquid flow conduit 118 according to a switching operation of the three-way electromagnetic valve 110. A liquid flow pump 119, which is a self-priming type pump that can transfer only liquid and is excellent in a transfer ability of liquid, is interposed on the other end side of the liquid flow conduit 118.

A circulation port 156 disposed in a cleaning and disinfecting tub 104 is connected to one end of a circulation conduit 120. The other end of the circulation conduit 120 branches into two to communicate with the other end of the liquid flow conduit 118 and one end of a channel conduit 121. The other end of the channel conduit 121 communicates with respective connectors 133.

In the channel conduit 121, a channel pump 126, a channel block 127, and a channel electromagnetic valve 128 are respectively interposed in order from one end side halfway in the conduit. The other end of a conduit for case 130, one end of which is connected to a cleaning case 106, is connected to the channel conduit 121 between the channel block 127 and the channel electromagnetic valve 128. A relief valve 136 is interposed in the conduit for case 130. Note that the channel pump 126 is configured of a self-priming type pump, which can transfer both of liquid and gas at higher pressure than a non-self-priming type pump.

A detergent nozzle 122 is connected to one end of a cleaning agent conduit 139. The other end of the cleaning agent conduit 139 is connected to a detergent tank 111a. A pump for detergent 140 configured of a high-pressure self-priming type pump for lifting a cleaning agent from the detergent tank 111a to the cleaning and disinfecting tub 104 is interposed halfway in the cleaning agent conduit 139.

An alcohol tank 111b is connected to one end of an alcohol conduit 141. The alcohol conduit 141 is connected to the channel block 127 to communicate with the channel conduit 121 in a predetermined manner.

In the alcohol conduit 141, an alcohol supply pump 142 configured of a high-pressure self-priming type pump for lifting alcohol from the alcohol tank 111b to the cleaning and disinfecting tub 104 and an electromagnetic valve 143 are interposed.

One end of an air conduit 144 for supplying air from an air pump 145 configured of a self-priming type pump, which can transfer gas, is connected to the channel block 127 to communicate with the channel conduit 121 in a predetermined manner. The other end of the air conduit 144 is connected to the air pump 145. A check valve 147 and an air filter 146, which is periodically replaced, are interposed in a halfway position of the air conduit 144. In a discharge port 155 provided in the cleaning and disinfecting tub 104, a not-shown open-closable valve body for discharging a cleaning solution or the like to an outside and collecting a disinfection solution to the medicinal solution tank 158 according to a switching operation of the valve is provided.

The discharge port 155 is connected to the other end of a liquid discharge conduit 159, one end of which is connected to and communicates with a not-shown liquid discharge hose connected to an external liquid discharge port. A water discharge pump 160 configured of a non-self-priming type pump is interposed in the liquid discharge conduit 159. The discharge port 155 is connected to one end of a medicinal solution recovery conduit 161. The other end of the medicinal solution recovery conduit 161 is connected to the medicinal solution tank 158.

The medicinal solution tank 158 is connected to one end of a medicinal-solution supply conduit 162 as well such that a disinfection solution is supplied to the medicinal solution tank 158 from medicinal solution bottles 112a and 112b.

The one end portion of a medicinal solution conduit 164, at one end of which a suction filter 163 is provided, is housed in the medicinal solution tank 158 in a predetermined manner. The other end of the medicinal solution conduit 164 is connected to a disinfection solution nozzle 123. A high-pressure self-priming type pump 165 for lifting a disinfection solution from the medicinal solution tank 158 to the cleaning and disinfecting tub 104 is interposed in a halfway position of the medicinal solution conduit 164.

Further, as explained above, the pressure resistant container 20 is connected to the medicinal solution tank 158 via the medicinal-solution lead-in section 21 and the medicinal-solution lead-out section 22.

Note that, for example, two vibrating sections 152 and a heater 153 are disposed in a lower part of a bottom surface of the cleaning and disinfecting tub 104. For temperature adjustment of the heater 153, a temperature detection sensor 153a is provided substantially in a center of the bottom surface of the cleaning and disinfecting tub 104.

A power supply 171, to which electric power is supplied from an external AC receptacle, and a control section 170 electrically connected to the power supply 171 are provided on an inside of the endoscope reprocessor 100.

Note that the configuration of the endoscope reprocessor explained above with reference to FIG. 13 is only an example and is not limited to the configuration. The endoscope reprocessor can also be applied to a sterilization apparatus and the like in which a medicinal solution is used.

Third Embodiment

Figure 16:
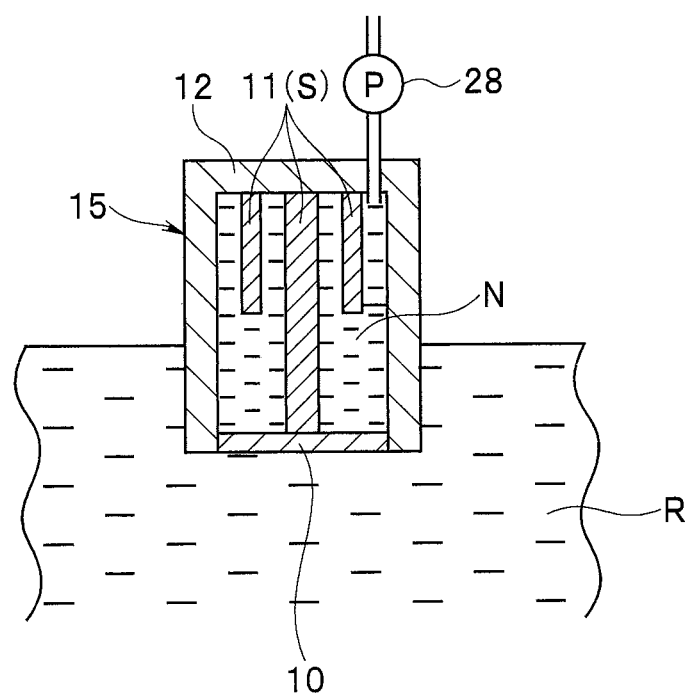
FIG. 16 is a diagram schematically showing a configuration of an endoscope reprocessor of a third embodiment.

FIG. 16 is a diagram schematically showing a configuration of an endoscope reprocessor of a third embodiment.

The endoscope reprocessor of the first embodiment shown in FIGS. 1 and 2 includes, as the pressure adjusting section, the pressurizing section 25 configured to pressurize the pressure resistant container 20. A concentration measuring device of the third embodiment is different in that the concentration measuring device includes, as a pressure adjusting section, a decompressing section 28 configured to reduce an internal pressure in the concave section 12 of the concentration sensor 15.

Means configured to reduce the internal pressure in the concave section 12 is not particularly limited. For example, in FIG. 16, a pump is illustrated as the decompressing section 28. However, the decompressing section 28 is not limited to this. Publicly-known decompressing means can be applied.

By reducing the internal pressure of the concave section 12, it is possible to reduce the internal pressure of the concave section 12 compared with the pressure resistant container 20. As a result, it is possible to facilitate permeation of the medicinal solution R into the permeable membrane 10.

Although not shown in FIG. 16, the concentration sensor 15 may include a pressure measuring section configured to measure the internal pressure of the concave section 12. In this case, the pressure measuring section and the decompressing section 28 are desirably connected to the control section. The decompressing section 28 is driven on the basis of a measurement result of the pressure measuring section.

Although not shown in FIG. 16, it is desirable that the endoscope reprocessor includes a structure for returning the reduced internal pressure of the concave section 12 to a predetermined pressure. The endoscope reprocessor may include, for example, an opening for opening the concave section to atmosphere and an on-off valve configured to open and close the opening. As another example, the endoscope reprocessor may include a normal and reverse rotation pump as the decompressing section 28.

Note that the present embodiment can be used concurrently with the first and second embodiments.

Further, the present embodiment is also applicable to detection of components other than the disinfection solution. The present embodiment is not limited to the detection of the peracetic acid concentration in the medicinal solution and is also applicable to oxygen concentration detection in the medicinal solution, detection of a pH value, and the like.

In the first, second, and third embodiments explained above, in the concentration sensor 15, the internal solution N is sealed in the concave section 12 by the permeable membrane 10. The electrode 11 is explained as the example of the sensing section S provided in the concave section 12. However, independently of this, the first, second, and third embodiments are applicable if the internal solution N is not provided in the concave section 12 and, for example, a gas detection sensor is used as the sensing section S.

When the gas detection sensor is used as the sensing section, it is desirable that air not including a measurement target component or relatively stable nitrogen or rare gas is filled in the concave section 12 instead of the internal solution N.

What is claimed is:

1. An endoscope reprocessor comprising:
   a concave housing;
   a concentration sensor disposed in the concave housing, the concentration sensor being configured to detect a fluid concentration in the concave housing;
   a permeable membrane configured to cover the concave housing;

a pressure resistant container in which at least a portion of the concave housing is housed;

a medicinal-solution lead-in conduit configured to introduce a medicinal solution into the pressure resistant container; and a controller, comprising hardware, the controller being configured to adjust pressure such that an internal pressure of the concave housing is low compared with an internal pressure of the pressure resistant container.

2. The endoscope reprocessor according to claim 1, wherein the controller is configured to increase the internal pressure of the pressure resistant container to a predetermined pressure.

3. The endoscope reprocessor according to claim 1, wherein the controller is configured to reduce the internal pressure of the concave housing to a predetermined pressure.

4. The endoscope reprocessor according to claim 1, wherein an internal solution is sealed in the concave housing by the permeable membrane, and the concentration sensor comprises an electrode, at least a part of which is immersed in the internal solution, the electrode being configured to be applied with a constant voltage to measure a concentration of the medicinal solution in the concave housing, the medicinal solution permeating through the permeable membrane, using an electrochemical reaction between the electrode and the internal solution.

5. The endoscope reprocessor according to claim 1, further comprising a medicinal solution tank in which the medicinal solution is stored, wherein the medicinal-solution lead-in conduit connects the medicinal solution tank and the pressure resistant container and supplies the medicinal solution in the medicinal solution tank to the pressure resistant container.

6. The endoscope reprocessor according to claim 5, wherein the medicinal-solution lead-in conduit includes a medicinal-solution pump configured to transfer the medicinal solution in the medicinal solution tank, and the medicinal solution in the medicinal solution tank is supplied to the pressure resistant container following driving of the medicinal-solution pump.

7. The endoscope reprocessor according to claim 2, further comprising:

a medicinal-solution lead-out conduit provided in the pressure resistant container; and a flow-rate limiting valve provided in the medicinal-solution lead-out conduit, the flow-rate limiting valve being configured to limit a flow rate of fluid led out from the pressure resistant container, and the controller limits the flow rate of the fluid led out from the pressure resistant container by the flow-rate limiting valve to be smaller than a flow rate of the medicinal solution introduced into the pressure resistant container from the medicinal-solution lead-in conduit, whereby the internal pressure of the pressure resistant container rises.

8. The endoscope reprocessor according to claim 7, wherein the flow-rate limiting valve is a relief valve opened when the internal pressure of the pressure resistant container reaches the predetermined pressure.

9. The endoscope reprocessor according to claim 7, further comprising:

a dryness detecting sensor configured to detect a dryness degree of the permeable membrane;

wherein the controller is connected to the flow-rate limiting valve, the controller being configured to determine whether the permeable membrane reaches a predetermined dry state based on a detection result of the dryness detecting sensor; and when the controller determines that the permeable membrane is dry, the controller controls the flow-rate limiting valve to limit the flow rate of the fluid led out from the pressure resistant container to be smaller than the flow rate of the medicinal solution introduced into the pressure resistant container from the medicinal-solution lead-in conduit.

\* \* \* \* \*